United States Patent [19]

Goldberg et al.

[11] Patent Number: 4,671,954

[45] Date of Patent: Jun. 9, 1987

[54] MICROSPHERES FOR INCORPORATION OF THERAPEUTIC SUBSTANCES AND METHODS OF PREPARATION THEREOF

[75] Inventors: Eugene P. Goldberg; William E. Longo, both of Gainesville, Fla.; Hiroo Iwata, Suita, Japan

[73] Assignee: University of Florida, Gainesville, Fla.

[21] Appl. No.: 825,789

[22] Filed: Feb. 4, 1986

Related U.S. Application Data

[63] Continuation of Ser. No. 560,952, Dec. 13, 1983, abandoned.

[51] Int. Cl.⁴ .......................... A61K 9/52; A61K 9/64; B01J 13/02
[52] U.S. Cl. ..................................... 424/450; 264/4.3; 424/1.1; 424/491; 428/402.2; 436/829; 514/34; 514/37; 514/963
[58] Field of Search ...................... 264/4.3; 428/402.2; 424/19, 36; 436/829

[56] References Cited

U.S. PATENT DOCUMENTS

| | | | |
|---|---|---|---|
| 3,208,994 | 9/1965 | Flodin | 536/112 |
| 3,532,662 | 10/1970 | Ansdell | 524/923 |
| 4,062,799 | 12/1977 | Matsukawa et al. | 428/402.2 X |
| 4,107,288 | 8/1978 | Oppenheim et al. | 264/4.3 X |
| 4,115,534 | 9/1978 | Ithakissios | 427/213.3 X |
| 4,147,767 | 4/1979 | Yapel, Jr. | 428/402.24 X |
| 4,342,739 | 8/1982 | Kakimi et al. | 428/402.21 X |
| 4,357,259 | 11/1982 | Senyei et al. | 252/62.54 X |
| 4,376,059 | 3/1983 | Davis et al. | 264/4.3 |

OTHER PUBLICATIONS

A. F. Yapel, Jr.: "Albumen Microspheres: Heat and Chemical Stabilization", *Methods in Enzymology,* vol. 112, Drug and Enzyme Targeting, Part A, edited by K. J. Widder et al., (1985), Academic Press, Inc., pp. 3–18.

*Primary Examiner*—Richard D. Lovering
*Attorney, Agent, or Firm*—Dennis P. Clarke

[57] ABSTRACT

Novel hydrophilic protein or polypeptide microspheres prepared by dispersing an aqueous solution or dispersion of protein or polypeptide in an organic solvent solution of a high molecular weight polymer to form a stabilized dispersion of microspheres and cross-linking said microspheres with a polyfunctional cross-linking agent.

30 Claims, No Drawings ically active or other substances and a method for
MICROSPHERES FOR INCORPORATION OF THERAPEUTIC SUBSTANCES AND METHODS OF PREPARATION THEREOF This is a continuation of application Ser. No. 560,952, filed Dec. 13, 1983 and now abandoned.

BACKGROUND OF THE INVENTION

Insoluble polypeptide or protein microspheres containing therapeutic agents which enable the controlled release thereof in biological systems have generated growing interest in recent years [Kramer, J. Pharm. Sci., 63, page 1646 (1976); Widder et al: Cancer Research, 40, page 3512 (1980) and Widder et al; J. Pharm. Sci., 68, page 79 (1979)]. Systems utilizing the microspheres have the potential advantage of prolonging effective drug concentrations in the blood stream or tissue when injected thereby reducing the frequency of administration; localizing high drug concentrations; reducing drug toxicity, and enhancing drug stability. Albumin is a preferred protein or polypeptide for the preparation of such microspheres since it is a naturally occurring product in human serum. Although it is usually necessary to cross-link the albumin when preparing microspheres according to conventional methods cross-linked albumin may still be degraded depending upon cross link density thereby enabling the use thereof for drug delivery systems, etc.

Conventional methods for the preparation of albumin microspheres are generally of two types. In one method, aqueous dispersions of albumin are insolubilized in vegetable oil or isooctane or other hydrocarbon solvent by denaturing at elevated temperatures (110°–165° C.). Another method involves chemical cross-linking of the aqueous dispersion of albumin at room temperature. Typical of these two types of methods are those described in U.S. Pat. Nos. 4,147,767; 4,356,259; 4,349,530; 4,169,804; 4,230,687; 3,937,668; 3,137,631; 3,202,731; 3,429,827; 3,663,685, 3,663,686; 3,663,687; 3,758,678 and Ishizaka et al, J. Pharm. Sci., Vol. 20, page 358 (1981).

These methods, however, result in the formation of relatively hydrophobic microspheres which usually require a surfactant in order to disperse a sufficient quantity thereof in water or other systems for administration to a biological system to ensure the delivery thereto of an effective amount of any biologically active agent entrapped therein. In addition, the hydrophobic nature of conventional polypeptide microspheres make it extremely difficult to "load" large quantities of water soluble biologically active agents or other material within the microspheres after synthesis.

It is an object of the present invention to provide more hydrophilic polypeptide microspheres which will accept high "loadings" of biologically active substances or other materials especially by addition of such substances after microsphere synthesis, and to prepare such drug loaded microspheres which do not require the utilization of surfactants to enable the preparation of highly concentrated dispersions thereof.

It is a further object of the invention to provide hydrophilic microspheres which may be more readily modified by aqueous chemical methods to covalently attach proteins, enzymes, antibodies, immunostimulants, and other compounds to alter and improve microsphere properties.

It is a further object of the present invention to provide a novel method for the preparation of such hydrophilic microspheres.

It is still a further object of the present invention to provide novel hydrophilic microspheres containing biologically active or other substances and a method for the preparation thereof.

It is still a further object of the present invention to provide a composition for administration to an animal, including humans, comprising the novel hydrophilic polypeptide microspheres containing a biologically active substance.

It is still a further object of the present invention to provide a novel method for administering a biologically active substance to an animal based upon a system comprising hydrophilic polypeptide microspheres containing a biologically active substance.

SUMMARY OF THE INVENTION

The foregoing and other objects of the invention are provided by novel hydrophilic microspheres prepared by a method comprising (a) providing a dispersion of an aqueous solution or dispersion of polypeptide or protein microspheres in an organic substantially water immiscible solvent solution of high molecular weight polymer wherein the organic solvent is substantially a non-solvent for the protein microspheres and the soluble polymer stabilizes the protein or polypeptide microsphere dispersion.

(b) incorporating a polyfunctional cross-linking agent for the protein or polypeptide in the dispersion, and (c) allowing the cross-linking agent to react with the protein or polypeptide microspheres for a time sufficient to cross-link at least a portion of the microspheres and, thereby to render the microspheres substantially insoluble in water and to provide free reactive functional groups therein.

The present invention also provides novel cross-linked hydrophilic polypeptide microspheres containing additional substances prepared by reacting the free reactive functional groups of the above-described cross-linked protein microspheres with substances containing at least one functional group reactive therewith to form a covalent or other type of bond between the cross-linked protein microspheres and the additional substance.

The present invention also provides a composition in unit dosage form adapted for administration to a biological system comprising a biologically effective amount of the above-described cross-linked hydrophilic polypeptide microspheres bonded with a biologically active substance.

The present invention also provides a method of administering a biologically active substance to a biological system comprising administering thereto a biologically effective amount of the above-described composition.

DETAILED DESCRIPTION OF THE INVENTION

The present invention is predicated on the discovery that more hydrophilic protein or polypeptide microspheres can be prepared than heretofore if an aqueous polypeptide or protein solution is first dispersed in organic solvent solutions of certain high molecular weight polymers wherein the organic solvent is a non-solvent for the aqueous polypeptide. The resulting dispersion comprises a polypeptide or protein solution dispersed in a high molecular weight polymer solution in an organic solvent external phase. This polymer solution functions to stabilize the aqueous protein or polypeptide dispersion and ensures the integrity of the individual microspheres.

When a polyfunctional cross-linking agent is introduced into this dispersion, preferably in the form of an organic solvent solution, the cross-linking agent is presented initially to the external surfaces of the microspheres rather than to the interior thereof as in the conventional prior art methods for microsphere production, thereby creating a relatively higher cross-link density at the surfaces of the microspheres than in the interior. This phenomenon also gives rise to a high concentration of free reactive functional groups from the cross-linking agent at the surface of the microspheres thereby facilitating increased hydrophilicity thereof especially if the microspheres are allowed to react with an added reagent reactive therewith, e.g., an amino acid or amino alcohol. The availability of these free amino acid or amino alcohol functional groups for reaction with other substances containing functional groups reactive therewith also renders the microspheres capable of being much more highly "loaded" with additional substances such as therapeutically active agents, etc., than conventional microspheres.

Moreover, the more hydrophilic nature of the microspheres enhances their dispersion in aqueous media, thereby enabling the safe administration thereof to animals, including humans, or other biological systems in much greater amounts than conventional hydrophobic microspheres, which require the presence of possibly biologically deleterious amounts of surfactants to achieve similar concentrations of administrable microspheres.

It will be understood by those skilled in the art, having been exposed to the principles of the present invention, that any protein or polypeptide capable of forming a cross-linked microsphere may be employed in the practice of the invention. Suitable such proteins or polypeptides include serum albumin, poly-L-lysine, poly-L-arginine, poly-L-histidine, polyglutamic acid, and any water soluble protein with functional amine groups such as enzymes, immunoglobulins, etc.

Furthermore, other polypeptides or macromolecules may be incorporated into the albumin microspheres even if they do not participate in the cross-linking reaction. These may be added to the albumin in the aqueous phase in concentrations ranging from 0.1 to 30%, by weight, or more and become entrapped during the cross-linking process. Such added macromolecules include, for example, polyglutamic acid, carboxymethyl dextran, carboxymethyl cellulose, polygalacturonic acid, cellulose, dextran, etc.

Where microspheres are to be subsequently reacted with a biologically active substance to produce a composition suitable for administration to a biological system, it is preferred to utilize an albumin to form the microsphere since it is a naturally occurring substance in most biological systems. Moreover, albumin, which has been cross-linked with most polyfunctional reagents, may be degraded in vivo, depending upon the extent of cross-linking, after administration to a biological system. Although any form of albumin may be used in the practice of the invention it is preferred to match the albumin with the biological system to which microspheres prepared therefrom are administered, e.g., human serum albumin, bovine serum albumin, rabbit serum albumin, fatty acid free human serum albumin, dog serum albumin, egg albumin, horse serum albumin, etc.

The aqueous solution or dispersion of protein or polypeptide is first dispersed in an organic solvent solution of a high molecular weight polymer.

Any polymer capable of forming a stabilized dispersion of the protein or polypeptide may be utilized in the practice of the invention. The polymer solution should be one which stabilizes the resulting dispersion of microspheres in the organic solvent/aqueous external phase against coagulation, agglomeration, etc. Suitable such polymers include, for example, acrylic polymers, e.g., polymethylmethacrylate, etc., polyoxyethylenepolyoxypropylene block copolymers, cellulose acetatebutyrate, polycarbonates, e.g., bisphenol polycarbonate, etc., polysulfones, polyacrylamides, polyvinyl alcohols, polyacetals, polystyrene and copolymers thereof, polyesters, polyamides, etc.

The organic solvent for the polymer should be a non-solvent for the aqueous protein or polypeptide solution and inert with respect thereto and capable of forming at least a 1–40%, by weight, solution of the polymer. Suitable solvents will depend, of course, upon the particular protein or polypeptide used to form the microspheres and the stabilizing polymer. Having been exposed to the principles of the present invention those skilled in the art will be able to determine suitable polymers and organic solvents without the exercise of inventive faculties or undue experimentation. Typical of useful organic polymer solvents are toluene, benzene, chloroform, ethylene dichloride, methylene chloride, etc., and mixtures thereof.

The term "microsphere" is intended to include any small particles of protein or polypeptide or mixture thereof with other macromolecules of generally spherical shape which is formed upon dispersion of an aqueous solution of protein or polypeptide in an organic solvent solution of a stabilizing polymer.

The stabilization of the microspheres is largely dependent upon the concentration and molecular weight (M.W.) of the polymer in the organic solvent. Generally, as the M.W. of the polymer is increased, the concentration of said polymer can be decreased. The upper limit of polymer concentration is governed by the ease of removal of the polymer after microsphere cross-linking. Generally, concentrations between about 10% and 30%, by weight, depending upon the particular protein or polypeptide and polymer selected, will be sufficient to produce suitable dispersions.

Average size and size distribution of the microspheres is usually a function of the shear forces and the time, i.e., energy, necessary to prepare the dispersions. Increasing either the shear forces or time of dispersion or both decreases the size of the microspheres. Generally, when producing large microspheres, a lower polymer concentration may be used. Smaller microspheres usually require higher polymer concentrations and more dilute protein dispersions.

Microspheres having a size in the range of from about 0.05 micron to about 500 microns may be prepared according to the method of the invention. Those skilled in the art having been exposed to the principles of the invention as described herein will be capable of selecting appropriate polymer concentrations and molecular weights and dispersion techniques to prepare microspheres of a desired size without the exercise of inventive faculties and undue experimentation.

Suitable cross-linking agents include polyfunctional reagents capable of reacting with the functional groups, particularly the amino groups, present on the protein or polypeptide to cross-link the molecules thereof. The selection of a particular cross-linking agent will depend to a large extent upon the intended use of the microspheres. Generally, however, any polyfunctional reagent, including those used heretofore in prior art methods to cross-link proteins, may be utilized to form the microspheres of the present invention. Typical of such reagents are polyaldehydes such as glutaraldehyde and polyisocyanates such as 2,4-tolylenediisocyanate, 1,6-diisocyanatohexane and activated polyfluoro compounds such as 1,5-difluoro-2,4-dinitrobenzene and P,P'-difluoro-m,m'-dinitrodiphenylsulfone.

The cross-linking agent is preferably presented to the microspheres by incorporating in the above-described dispersion of protein or polypeptide microspheres an organic solvent solution of the cross-linking agent. The organic solvent for the cross-linking agent is one that is compatible with the solvent for the organic polymer and is likewise a non-solvent for the microspheres. The cross-linker diffuses into the microspheres from the organic phase with consequent increased concentration at the surfaces thereof. As a result, the other surfaces of the microspheres are usually cross-linked to a greater extent than the exterior portions.

This is in contrast to conventional prior art methods wherein the cross-linker is usually present in the aqueous protein dispersion thereby resulting in substantially uniform cross-linking throughout the microspheres. In addition, there is a larger concentration of free functional groups at the outer surfaces of the microspheres of the present invention as a result of some reactions between only one of the functional groups of the cross-linkder with amino groups of protein or polypeptide molecules.

These free reactive functional groups (e.g., aldehyde groups, where the cross-linker is a polyaldehyde) at the surface render the microspheres more hydrophilic and readily susceptible to wetting and dispersion in aqueous media, especially when further reacted with polar compounds such as amino acids or amino alcohols or when oxidized to carboxylic groups.

Suitable organic solvents for the cross-linking agent include any which are non-solvents for the microspheres and which are compatible with the solvent for the organic polymer and the cross-linking agent. Suitable solvents include those listed above as suitable for solubilizing the polymer. Those skilled in the art, having been exposed to the principles of the present invention, will be capable of selecting suitable solvents for the cross-linkers without the exercise of inventive faculties or undue experimentation.

The cross-link density as well as the number of free functional groups at the surfaces of the microspheres can be controlled by regulating the concentration of the cross-linking agent. Generally, as the concentration of cross-linker in the final dispersion is increased, the cross-link density and the number of free functional groups at the outer surfaces of the microspheres are increased. For most applications, a sufficient quantity of cross-linker solution is added to the microsphere dispersion to yield a final cross-linker concentration therein of between about 0.1% and about 25%, by weight. It will be understood, however, that any concentration consistent with an efficient completion of the method and the intended use of the microspheres may be utilized.

The following non-limiting examples are illustrative of the novel microspheres of the present invention and of methods for their preparation and use.

Preparation of glutaraldehyde cross-linked human serum albumin(HSA) microspheres(MS)

EXAMPLE 1

HSA (0.150 g) (Sigma, recrystallized and lyophilized) was dissolved in 0.5 ml water in a 16×125 mm test tube (this size test tube was used throughout all of the following procedures except where noted). The solution was added drop wise to a 25 wt % solution of polymethylmethacrylate (PMMA) (Polyscience, intrinsic viscosity 1.4) in a mixture of 1.5 ml chloroform and 1.5 ml toluene in a screw cap test tube. The mixture was dispersed with a vortex mixer (Vortex Genie Scientific Industries, Inc.) for two minutes at a power setting of nine. Aqueous glutaraldehyde 1.0 ml (25 wt%) and 1.0 ml of toluene were combined in a 13×100 mm test tube. The two phases were dispersed by ultrasonification (Heat Systems-Ultrasonics, Model W-375) with a microtrip power head attachment (20 sec. at 50 watts). The resulting toluene solution of glutaraldehyde, (0.14 mmoles) was allowed to phase separate, pipeted off, and combined with the albumin dispersion. After addition of the glutaraldehyde saturated toluene, the albumin dispersion was mixed with a rotary mixer (Labquate Labindustries) at room temperature (r.t.) for 8 hrs. The resulting cross-linked HSA/MS were washed to remove all PMMA dispersant by the addition of 10.0 ml of acetone, test tube briefly agitated, then centrifuged (2000 RPM×2 min.), the supernate discarded and the HSA/MS-U pellet re-suspended with an additional 10.0 ml of acetone. This wash procedure was repeated eight times. After the last wash, HSA/MS were allowed to air dry. The product was a brown powder, 0.122 g, 81% yield. The average diameter of the HSA/MS was 29 μm as determined by optical microscopy.

EXAMPLE 2

HSA (0.150 g) was dissolved in 0.5 ml of water in a test tube. This solution was added dropwise to a 25 wt % solution of polyoxyethylene/polyoxypropylene copolymer (Poloxmer 188 (BASF Wyandotte Corp., MW 8430)) in 4.0 ml chloroform in a screw cap test tube. The mixture was dispersed with a vortex mixer for two minutes at power setting nine. Glutaraldehyde was used for cross-linking and was prepared with chloroform by sonification as previously described in Example 1. After addition of the glutaraldehyde saturated chloroform, the albumin dispersion was mixed with a rotary mixer at r.t. for 6 hrs. The resulting cross-linked HSA/MS were washed to remove all Poloxmer 188 dispersant as described in Example 1. The MS product was a brown powder, 0.115 g, 77% yield. The average diameter was 20-40 μm, as determined by optical microscopy.

EXAMPLE 3

HSA (0.150 g) was dissolved in 0.5 ml of water in a test tube. This solution was added dropwise to a 3.0 wt % solution of cellulose acetate butyrate (CAB Polyscience, MW 73,000) in 4.0 ml of ethylene dichloride in a screw cap test tube. The mixture was dispersed with a vortex mixer for two minutes at power setting nine. Glutaraldehyde was used for cross-linking and was prepared as described in Example 1. After addition of the glutaraldehyde saturated toluene, the dispersion was mixed with a rotary mixer at r.t. for 24 hrs. The resulting cross-linked HSA/MS were washed to remove all CAB dispersant and dehydrated as described in Example 1. The MS product was a brown powder, 0.11 g, 73% yield. The average diameter was 25 μm determined by optical microscopy.

EXAMPLE 4

HSA (0.156 g) was dissolved in 0.5 ml of water in a test tube. This solution was added dropwise to a 20 wt % solution of bisphenyl polycarbonate (General Electric, MW 32,000) in 4.0 ml of chloroform. Glutaraldehyde was used for cross-linking and was prepared as described in Example 2. After addition of the glutaraldehyde saturated chloroform, the mixture was mixed with a rotary mixer at r.t. for 16 hrs. The resulting cross-linked HSA/MS were washed to remove all polycarbonate dispersant by the addition of chloroform (8 X, 10.0 ml volumes), then acetone (8 X, 10.0 ml volumes) and water (4 X, 5.0 ml volumes). After the water wash, MS were examined with an optical microscope and stored frozen at 0° C. Average diameter of the MS were 10–50 μm.

EXAMPLE 5

Human Serum Albumin (Fatty Acid Free (FAF) Microspheres-Unquenched

HSA(FAF) (0.145 g, Sigma) was dissolved in 0.5 ml of water in a test tube. This solution was dispersed in the PMMA solution and cross-linked with glutaraldehyde for 16 hrs as described in Example 1. MS were washed to remove all PMMA dispersant by centrifugation with acetone (8X) then water (4X). After the last water wash the HSA(FAF)MS pellet was re-suspended in 10.0 ml of water. Aliquots (0.5 ml) were removed from the well-shaken sample and pipeted into three pre-weighed 13×100 mm test tubes, then placed in a 100 C. oven (National) to remove all water. Test tubes were cooled to r.t. and weighed, average of the three weights being used to determine the weight of MS per ml of water in the 10.0 ml volume. This yield was 0.114 g, 79% of HSA(FAF)MS. The average diameter of the MS was 32 μm as determined by optical microscopy.

EXAMPLE 6

Bovine, Dog and Rabbit Serum Albumin/Microspheres-Unquenched

Bovine serum albumin (BSA) (0.150 g), dog serum albumin (DSA) (0.150 g) and rabbit serum albumin (RSA) (0.150 g) obtained from Sigma (fraction V) were dissolved in 0.5 ml of water in test tube. The albumin/MS were then synthesized as described in Example 1 with a cross-linking reaction time of 16 hrs. The MS were washed with acetone, (8X, 10.0 ml volumes) to remove all PMMA, then with water (4X, 5.0 ml volumes). After the last water wash the brown pellets were re-suspended in 10.0 ml of water, and weight of albumin/MS per ml was determined as described above. The yield was 0.109 g, 73% (2) 0.103 g, 69% and (3) 0.128 g, 82%. Average diameter of MS were 28, 14 and 13 μm, respectively, as determined by optical microscopy. The MS are readily formed and are similar to MS produced from human albumin. This demonstrates the versatility of the procedure and the ability to synthesize MS from other mammelian protein which would be beneficial for veterinary applications when MS containing therapeutic agents are required.

EXAMPLE 7

Polylysine (PLY)/Microspheres-Unquenched

PLY (0.151 g, MS 11,000, 0.11 μmoles, Sigma) was dissolved in 0.5 ml of water in a test tube. This solution was dispersed in the PMMA mixture and PLY/MS were synthesized as described in Example 1 with a cross-linking reaction time of 2 hrs. The PLY/MS were washed with acetone to remove all PMMA, then with water. After the last water wash the yellow pellet was re-suspended in 10.0 ml of water and weight of the PLY/MS were determined as described above. This produced 0.120 g of PLY/MS in solution, 79% yield.

Polylysine (PLY) is a cationic polypeptide that consists of repeating units of amino residues with a net positive charge. PLY may be incorporated into the HSA matrix at various wt. concentrations. It is also possible to make PLY/MS. Glutaraldehyde was able to cross-link the PLY molecules in the same manner as albumin. PLY/MS would be advantageous because of its ability to conjugate acidic drugs by the formation of a salt complex.

EXAMPLE 8

Preparation of diisocyanate cross-linked bovine serum albumin(BSA) microspheres(MS)

BSA (0.161 g) was dissolved in 0.5 ml of water in a test tube. This solution was dispersed in the PMMA solution as described in Example 1. Tolylene 2,4-diisocyanate (TDI) (Aldrich) was used to cross-link the albumin. Aqueous TDT (80% 4.6 mmoles) 1.0 ml, and 1.0 ml of toluene were combined in a 2.0 ml volumetric flask. After mixing well, 1.0 ml of the TDI/toluene solution was added to the albumin dispersion. The dispersion was then mixed with a rotary mixer at r.t. for 21 hrs. BSA/MS were washed to remove all PMMA dispersant by centrifugation with acetone then water. After the water wash, the white pellet was frozen in liquid nitrogen and lyophilized yielding 0.246 g of MS as a dry, free flowing white powder.

EXAMPLE 9

BSA (0.163 g) was dissolved in 0.5 ml of water in a test tube. The solution was dispersed in the PMMA solution as described in Example 1. Aqueous 1,6-diisocyanatohexane (DCH) (98% Aldrich), 1.0 ml (5.8 mmoles) and 1.0 ml toluene were combined in a 2.0 ml volumetric flask. After mixing well, 1.0 ml of the resulting solution was added to the albumin dispersion and mixed at r.t. for 21 hrs. The BSA/MS were washed and dehydrated according to the procedure in Example 8. The MS product was a white powder, 0.023 g, 76% yield.

EXAMPLE 10

Synthesis of Sub-Micron Microspheres

HSA, 0.164 g, was dissolved in 0.5 ml of water and added dropwise to 3.0 percent CAB in 25 ml of ethylene dichloride in 25×150 mm screw cap culture tubes. The mixture was dispersed with a Brinkman Homogenizer (Pt 10-35) connected to a PT 20/TS probe generation at a setting of 6.5 for 10 mins. The dispersion was added dropwise to a 500 ml round bottom flask containing 100 ml of 3.0 percent CAB polymer solution and mixed at medium speed with a magnetic stirrer. A 4.0 ml glutaraldehyde saturated toluene solution was used for cross-linking (see Example 1) and the dispersion was allowed to react for 2 hrs at room temperature. The cross-linked MS were washed out with acetone and dehydrated as described in Example 1. This yield 0.094 g of dry MS powder. Average size of the MS, determined using the scanning electron microscope, was 0.9 μm. The size distribution is shown in Table 1.

TABLE 1

Sub-Micron: HSA/MS Size Distributions in CAB Dispersant
% Fraction

| Size/μm | Energy 6.5 Time (10 mins) |
|---|---|
| 0–0.5 | 6 |
| 0.5–0.75 | 49 |
| 0.75–1.0 | 13 |
| 1.0–1.25 | 19 |
| 1.25–1.5 | 10 |
| 1.5–1.75 | 3 |
| 1.75–2.0 | 0 |
| 2.0–4.5 | 0 |

EXAMPLE 11

Microspheres with Variations In Cross-Link Density and Hydration

BSA samples (1) 0.150 g, (2) 0.151 g (3) 0.150 g, and (4) 0.149 g were dissolved in 0.5 ml of water in test tubes. These solutions were dispersed in the PMMA mixture as described in Example 1. Glutaraldehyde was used for cross-linking and was diluted with water in the following ratios 1:1, 1:5, 1:10 and 1:20; this gave a final molar concentration of (a) 1.25 moles, (b) 0.5 mmoles, (c) 0.25 mmoles, and (d) 0.125 moles. The glutaraldehyde solutions were combined with toluene and dispersed as described in Example 1. After addition of the glutaraldehyde saturated toluene solutions (a) through (d) to the BSA/PMMA dispersions 1 through 4, they were mixed with a rotary mixer at r.t. for 22 hrs. After the final acetone wash and dehydration, the BSA/MS samples had a dry weight of (1) 0.125 g, (2) 0.140 g, (3) 0.135 g, and (4) 0.063 g. An aliquot of water (10.0 ml) was added to each sample and allowed to hydrate for 1.0 hr at room temperature. The dispersions were then centrifuged and all of the supernate was carefully removed with a pasteur pipet. BSA/MS were then re-weighed to determine water content and were as follows: (1) 0.579 g, (2) 0.881 g, (3) 1.55 g, and (4) 0.969 g, by dividing the net weight by the dry weight the water content per mg of BSA/MS was determined. Average diameter of the MS for both the dry state and wet state was determined by optical microscopy. See Table 2.

TABLE 2

Varying Cross-Link Density and Hydration of BSA/MS (Glutaraldehyde Cross-Linking)

| Glutaraldehyde Concentration (mmoles) | Mean Diameter Dehydrated (μm) | Mean Diameter Hydrated (μm) | mg Water Uptake/mg of BSA/HSA | % Hydration |
|---|---|---|---|---|
| 1.25 | 14 | 17 | 4.6 | 82 |
| 0.50 | 13 | 21 | 6.3 | 86 |
| 0.25 | 10 | 23 | 11.5 | 92 |
| 0.13 | 17 | 37 | 15.4 | 94 |

EXAMPLE 12

BSA samples (1) 0.151 g, (2) 1.157 g, (3) 0.148 g and (4) 0.150 g were dissolved in 0.5 ml of water in test tubes. These solutions were then dispersed in the PMMA mixture as described in Example 1. Dilutions of tolylene 2,4-diisocyanate (TDC) were used for cross-linking and were prepared as follows. In four 10.0 ml volumetric flasks; (a) 0.4 ml, (b) 0.2 ml, (3) 0.1 ml. and (d) 0.07 ml of TDC were diluted with toluene. This gave final molar concentrations of (a) 0.18 mmoles (b) 0.092 mmoles (c) 0.046 mmoles and (d) 0.031 mmoles. One ml of the TDC/toluene solutions (a) through (d) were added to the albumin dispersions 1 through 4. The dispersions were then mixed with a rotary mixer at r.t. for 22 hrs. After the final acetone wash and dehydration, the BSA/MS samples had a dry weight of (1) 0.176 g (2) 0.171 g (3) 0.149 g and (4) 0.150 g. After hydration and removal of excess water as described in Example 11, the BSA/MS samples were re-weighed; this yielded (1) 0.314 g (2) 0.643 g (3) 1.950 g and (4) 3.664 g. The water content of the MS were then calculated for each sample as described in Example 11. Average diameter of the BSA/MS for both the dry state and wet state were determined by optical microscopy. See Table 3.

TABLE 3

Varying Cross-Link Density and Hydration of BSA/MS (TID Cross-Linking)

| Concentration of TDI (mmoles) | Mean Diameter Dehydrated (μm) | Mean Diameter Hydrated (μm) | mg Water Uptake/mg of BSA/MS | % Hydration |
|---|---|---|---|---|
| 0.18 | 18 | 19 | 1.8 | 64 |
| 0.092 | 18 | 22 | 3.6 | 78 |
| 0.046 | 21 | 30 | 13 | 93 |
| 0.031 | 16 | 40 | 24 | 96 |

EXAMPLE 13

BSA samples (1) 0.150 g (2) 0.166 g (3) 0.151 g (4) 0.149 g and (5) 0.160 g were dissolved in 0.5 ml of water in test tubes. These solutions were then dispersed in the PMMA mixture as described in Example 1. Dilutions of 1,6-diisocyanatohexane (DCH) were used for cross-linking and were prepared as follows: In five 10.0 ml volumetric flasks; (a) 5.0 ml (b) 2.0 ml (c) 1.0 ml (d) 0.4 ml and (e) 0.2 ml of DCH were added and diluted with toluene. This gave final molar concentrations of (a) 2.9 mmoles (b) 1.16 mmoles (c) 0.58 mmoles (d) 0.23 mmoles and (e) 0.12 mmoles. One ml of the DCH/toluene solutions (a) through (e) were added to the albumin dispersions (1) through (5). The dispersions were then mixed with a rotary mixer at r.t. for 22 hrs. After the final acetone wash and dehydration, the BSA/MS samples had a dry weight of (1) 0.140 g (2) 0.150 g (3) 0.141 g (4) 0.129 g and (5) 0.144 g. After hydration and removal of excess water as described in Example 11, the BSA/MS samples were re-weighed; this yielded (1) 0.240 g (2) 0.593 g (3) 0.898 g (4) 2.006 g and (5) 2.854 g. The water content of the BSA/MS were then determined for each sample as described in Example 11. Average diameter of the BSA/MS samples for both the dry state and wet state were determined by optical microscopy. See Table 4.

TABLE 4

Varying Cross-Link Density and Hydration of BSA/MS (DCH Cross-Linking)

| Concentration of DCH (mmoles) | Mean Diameter Dehydrated (μm) | Mean Diameter Hydrated (μm) | mg Water Uptake/mg BSA/MS | % Hydration |
|---|---|---|---|---|
| 2.9 | 18 | 20 | 1.7 | 63 |

TABLE 4-continued

Varying Cross-Link Density and Hydration of BSA/MS (DCH Cross-Linking)

| Concentration of DCH (mmoles) | Mean Diameter Dehydrated ($\mu$m) | Mean Diameter Hydrated ($\mu$m) | mg Water Uptake/mg BSA/MS | % Hydration |
|---|---|---|---|---|
| 1.16 | 21 | 29 | 3.7 | 79 |
| 0.58 | 13 | 28 | 6.4 | 86 |
| 0.23 | 17 | 38 | 16.0 | 94 |
| 0.12 | 16 | 50 | 20.0 | 95 |

The free functional groups on the cross-linked microspheres are capable of reaction with a wide variety of substances containing functional groups reactive with those on the microspheres whereby the substance is covalently or otherwise boned to the microspheres. There is virtually no limit to the types of substances which can be bound to the microspheres in this manner. Thus, the microspheres may be reacted with aminoalcohols, e.g., 2-aminoethanol or amino acids, e.g., glycine, to enhance hydrophilicity; coupled with, e.g., amino group containing drugs (adriamycin) for administration to a biological system or covalently bonded to large protein molecules such as lectins, enzymes or antibodies. In addition, changes in surface functionability of the microspheres may be used to enhance tissue immobilization by covalent or physical binding for specific tissue targeting using biospecific affinity ligands, e.g., tumor-specific immune assay reagents.

Whereas protein and polypeptide microspheres containing entrapped or encapsulated substances prepared according to prior art methods are relatively hydrophobic requiring surfactants for dispersion in aqueous media and make post-forming aqueous chemical modification difficult, those of the present invention are hydrophilic, capable of dispersion in aqueous media in relatively large amounts without the necessity for surfactants and are readily useful for post-forming absorption of biologically active agents or chemical modification in aqueous media.

Where it is desired to couple the microspheres with a substance which does not contain a functional group reactible with any free functional group in the cross-linked microsphere, the latter may first be reacted with a linking or bridging agent which has at least one functional group capable of reacting with the free functional group in the microspheres and at least one additional functional group which will react with the desired surfactant to covalently bond it to the microsphere.

Suitable substances for chemical or physical bonding to the microspheres, depending, of course, upon the nature of the free functional groups thereon or the ability of the drug to naturally bind thereto include antitumor agents, e.g., adriamycin, bleomycin, chlorambucil, mitomycin C, etc., antibiotics, e.g., streptomycin, gentamycin, tobramycin, formycin A, etc., steroids, e.g., hydrocortisone phosphate, progesterone and other contraceptive hormones, etc.

The term "biological system" as employed herein, is intended to include any living system, e.g., lower animal, human, plant, etc., to which a biologically active substance may be administered for therapeutic, diagnostic or other biological purpose.

The following non-limiting examples illustrate the embodiment of the invention wherein the microspheres are bonded physically or chemically (covalently) to substances. Physical binding or association of drugs occurs readily with albumin and is satisfactory for many types of albumin-drug microsphere systems, especially where rapid drug release is desired. Chemical binding occurs via available reactive functional groups. In the following examples, the term "quench" refers to the reaction of free functional groups in the interior and/or on the surface of the microspheres with a substance containing a functional group reactive therewith.

EXAMPLE 14

Measurement of Free Reactive Aldehyde Groups in Microspheres

Tritiated Leucine

HSA/MS (10 $\mu$m average diameter) were prepared as described in Example 1. The cross-linked HSA/MS were divided into two samples. One was quenched as described hereinbelow with 0.5 ml of 2-aminoethanol while the other sample was left unquenched. Tritiated leucine (New England Nuclear) specific activity 134.2$\mu$ Ci/mmoles/ml, was diluted with a L-leucine carrier to a final activity of 5$\mu$ curie/50 mmoles/ml. One ml of the isotope solution was added to each of three samples of 7.4 mg/ml unquenched and three samples of 8.0 mg/ml quenched MS in test tubes. The samples were incubated for 40 mins in a table top sonicator (E/MC RA Research), then washed four times with water by centrifugation (1000 RPM$\times$2 mins). MS pellets were re-suspended in 2.0 ml of a scintillation cocktail (Aquasol New England Nuclear). From each of the solutions 1.0, 0.5, and 0.25 ml aliquots were removed and added to scintillation counter containers. The final volumes were adjusted to 15.0 ml with additional cocktail solution. Activity was determined using a Beckman Model 230 scintillation counter and values plotted against prepared standards. See Table 5.

TABLE 5

Concentration of Reactive Aldehyde Groups for HSA/MS by Binding of Tritium Labeled Leucine

| Physical or Chemical Binding of Leucine | Leucine (moles) Bound/ml of MS | # of Leucine 10 $\mu$m MS | # Reactive CHO/MS* |
|---|---|---|---|
| HSA/MS-Quenched | 8.8 $\times$ 10$^{-2}$ | 5.5 $\times$ 10$^7$ | — |
| HSA/MS-Unquenched | 1.3 $\times$ 10$^{-1}$ | 7.8 $\times$ 10$^7$ | — |
| Chemically Reacted (MS-U - MS-Q) | 4.0 $\times$ 10$^{-2}$ | 2.4 $\times$ 10$^7$ | 2.4 $\times$ 10$^7$ |

*Assume one bound leucine equals one reactive aldehyde group.

EXAMPLE 15

Tritiated Concanavalin A (Con-A) Binding As a Function of Particle Size

HSA/MS samples were prepared as described in Example 1. This produced MS with an average diameter of 30 $\mu$m, 12 $\mu$m, and 5 $\mu$m. The cross-linked MS were divided into two samples, quenched and unquenched. Tritiated Con-A (New England Nuclear Corp.) specific activity 42.4$\mu$Cl/mmole/ml, was diluted with a carrier (Con-A, Sigma) to a final activity of 1.0$\mu$Ci/0.136$\mu$moles/ml, in 0.01 molar sodium phosphate buffer at pH 6.9. Two ml of the isotope solution was added to one sample of each particle size for both unquenched and quenched in test tubes. The samples were incubated for one hr in a table top sonicator, washed and re-suspended in a scintillation cocktail as described in Example 14. Activity was determined using a scintillation counter and values plotted against prepared standards. See Table 6.

TABLE 6

Con-A Binding to HSA/MS as a Function of MS Size

| Mean Diameter ($\mu$m) | Con-A ($\mu$moles) Bound/mg of HSA/MS-U | Con-A ($\mu$moles) Bound/mg of HSA/MS-Q | Reacted Con-A $\mu$moles/mg (U - Q) |
|---|---|---|---|
| 30 | $2.6 \times 10^{-4}$ | $2.6 \times 10^{-4}$ | 0 |
| 12 | $3.7 \times 10^{-4}$ | $3.2 \times 10^{-4}$ | $0.5 \times 10^{-4}$ |
| 5 | $6.7 \times 10^{-4}$ | $4.0 \times 10^{-4}$ | $2.7 \times 10^{-4}$ |

EXAMPLE 17

Physical Analysis of Surface Properties of Microspheres, Capillary Wetting as a Function of Quenching HSA/MS (30 $\mu$m average diameter) were prepared as described in Example 1. The HSA/MS were divided into two samples. One was quenched with glycine, as described hereinbelow, and the other sample was left unquenched, HSA/MS were dehydrated with acetone and air dried. Pasteur pipets (10 cm $\times$ 1 mm I.D.) were used as the capillary column. By gently pushing the pipet through a glass fiber (3 cm diameter, Gelman Type A-E) a plug was formed in the end of the column. HSA/MS samples were loaded into the column and packed by holding the capillary tube vertically on the rubber tip of the vortex genie, then vibrating the tube for 20 to 30 seconds at a speed setting of one, Columns were packed with HSA/MS to a height of 3.0 cm from top of glass fiber plug. The capillary tube was mounted vertically and placed in a PLEXIGLASS tank (10 cm $\times$ 10 cm $\times$ 5 cm filled with water) to a depth of one cm. The height of the water rise up the column was measured as a function of time. Both quenched and unquenched samples were run and the data taken (Table 7) was compared to HSA/MS produced by the prior art vegetable oil method (hydrophobic)

TABLE 7

Hydrophilic Measurements of HSA/MS as a Function of Surface Properties by Capillary Rise

| Time (mins) | HSA/MS Unquenched Height (mm) | HSA/MS Quenched Height (mm) | HSA/MS Hydrophobic Height (mm) |
|---|---|---|---|
| 15 | 2.4 | 9.4 | 0.1 |
| 35 | 2.7 | 13.7 | 0.1 |
| 45 | 2.9 | 17.2 | 0.1 |
| 60 | 3.2 | 20.1 | 0.1 |
| 75 | 3.4 | 22.5 | 0.1 |
| 90 | 3.5 | 24.9 | 0.1 |
| 105 | 3.7 | 26.8 | 0.1 |
| 120 | 3.8 | 28.6 | 0.1 |

EXAMPLE 18

Human Serum Albumin/Microspheres-Quenched (Q)

HSA/MS were synthesized and washed as described in Example 1. After the last acetone wash, the HSA/MS pellet was re-suspended with 5.0 ml of water, briefly agitated and centrifuged. This was repeated four additional times. After the last water wash, the HSA/MS pellet was re-suspended in 5.0 ml of 1.0 molar glycine HCl to "quench" the residual reactive aldehyde groups. The HSA/MS glycine solution was mixed at r.t. for 22 hrs with a rotary mixer. MS were removed from the unreacted glycine by centrifugation. After decanting the glycine supernate the HSA/MS pellet was re-suspended in a 50 ml polypropylene centrifuge tube (Corning) with 45.0 ml of water (pH 3.0), briefly agitated and centrifuged (2000 RPM $\times$ 2 min). This wash procedure was repeated three times. The process was repeated again with water at pH 7.0 After the last water wash, MS were dehydrated with acetone (4x, 100% acetone in 10.0 ml volumes) and allowed to air dry. The product was a yellowish brown powder, 115 g, 77% yield. The average size of the MS was 26 $\mu$m in diameter as determined with optical microscopy.

The following non-limiting examples illustrate the embodiment of the invention wherein other non-cross-linking substance (macromolecules) are entrapped in the albumin microsphere producing a composite of the albumin with the substance.

EXAMPLE 19

Human Serum Albumin/Microspheres Containing Polyglutamic Acid (PGA)-Unquenched

PGA (60,000 MW, Sigma) was added into HSA/MS in concentrations of 12, 16 and 22 wt %. The PGA-HSA/MS were synthesized, washed and dehydrated as described in Example 1. Samples were prepared with the following weight ratios of HSA and PGA:

| | HSA | PGA |
|---|---|---|
| 1. | 0.134 g | 0.017 g (0.3 $\mu$moles) |
| 2. | 0.129 g | 0.025 g (0.4 $\mu$moles) |
| 3. | 0.119 g | 0.032 g (0.5 $\mu$moles) |

The yields of the resulting cross-linked HSA/PGA/MS were as follows: (1) 0.117 g, 78% (2) 0.134 g, 87% and (3) 0.124 g, 82%. The average diameter of the microspheres were 34, 29, and 29 $\mu$m, respectively, as determined by optical microscopy.

EXAMPLE 20

Human Serum Albumin/Microspheres Containing Polyglutamic Acid-Quenched

HSA/PGA/MS were synthesized as described in Example 19. The amount of added PGA was 11, 15 and 19 wt %. The HSA/PGA/MS were then quenched with glycine to "cap" residual aldehyde groups. Samples were prepared with the following weight ratios of HSA and PGA:

| | HSA | PGA |
|---|---|---|
| 1. | 0.133 g | 0.016 g (0.30 $\mu$moles) |
| 2. | 0.127 g | 0.022 g (0.38 $\mu$moles) |
| 3. | 0.121 g | 0.029 g (0.48 $\mu$moles) |

The yields were as follows: (1) 0.115 g, 77% (2) 0.128 g, 85% and (3) 0.117 g, 78%. The average diameter of the microspheres were 23, 28, and 28 $\mu$m, respectively, as determined by optical microscopy.

Modification of Albumin Microspheres Cross-Linked with Tolylene 2,4-Diisocyanate (TDI)

EXAMPLE 21

Bovine Serum Albumin with 14% Polyglutamic Acid-Unquenched

BSA (0.131 g) and PGA (0.022 g) were combined and dissolved in 0.5 ml of water in a test tube. The albumin solution was dispersed in the PMMA mixture as described in Example 1. A 0.046 mmolar solution of TDI was prepared from 80% aqueous TDI and toluene. After mixing well, 1.0 ml of the solution was added to the albumin dispersion and mixed at r.t. for 12 hrs with a rotary mixer. BSA/MA were washed to remove all of the PMMA dispersant with acetone and dehydrated as described in Example 1. The product was a white powder, 0.146 g, 95% yield.

EXAMPLE 22

Bovine Serum Albumin with 14% Polyglutamic Acid Microspheres-Quenched

BSA (0.132 g) and PGA (0.021 g) were combined and dissolved in 0.5 ml of water in a test tube. The albumin solution was dispersed in the PMMA mixture, synthesized, washed and quenched as described in Example 18. The product was a white powder, 0.067 g, 44% yield.

EXAMPLE 23

Bovine Serum Albumin Microspheres Containing 11.7% Carboxymethyldextran (CMD)-Unquenched CMD was synthesized using the procedure of Pitha et al, J. Natl. Cancer Inst., Vol. 65, p. 5 (1980). Dextran (40,000 MW, Sigma) (5.0 g) was dissolved in 5.0 ml of water. This solution was added to 38 ml of 40% sodium hydroxide and 27 g of chloroacetic acid in a 125 ml Erlenmeyer flask. The suspension was stirred for 12.0 hrs at room temperature. After this process was repeated twice, the solution was extensively dialyzed against water using membrane tubing (Spectropor) with a 6,000–8,000 MW cutoff, inside diameter of the tubing was 25.5 mm. The modified dextran was frozen in liquid nitrogen and lyophilized. Yield of product was not recorded. The carboxylic content was 4.4 $\mu$moles of carboxyl groups per mg of material.

BSA (0.135 g) and CMD (0.018 g) were combined and dissolved with 0.5 ml of water in a test tube. The protein/dextran solution was dispersed in the PMMA mixture and the CMD-BSA/MS were synthesized as described above. The product was a white powder, 0.092 g, 60% yield.

EXAMPLE 24

Bovine Serum Albumin Microspheres Containing 15% Carboxymethyldextran-Quenched

BSA (0.139 g) and CMD (0.024 g) were combined and dissolved in 0.5 ml of water in a test tube. The protein/dextran solution was dispersed in the PMMA mixture and the CMD-BSA/MS were synthesized as described in Example 23. The CMD-BSA/MS were washed to remove all of the PMMA dispersant, quenched and dehydrated as described in Example 18. The product was white powder, 0.049 g, 30% yield.

The incorporation of PGA into HSA/MS increased anionicity. For applications (e.g. experimental treatment of Brucellosis in cattle) involving large scale production of anionic/MS, the use of PGA might be limited because of its high cost. A viable alternative to PGA is carboxymethyldextran (CMD). The modified dextran is inexpensive and has the physical properties (high content of functional carboxyl groups) required to increase anionicity of the albumin/MS.

EXAMPLE 25

18 wt % Adriamycin-Human Serum Albumin/Microspheres-Unquenched

Adriamycin in HCL (AD) (52.3 mg) (Farmitalia Carlo ERBA) was dissolved in 25.0 ml of water, 5.0 ml of the clear dark red solution (10.46 mg AD) was combined with 9.99 mg of the HSA/MS-U (synthesized in Example 1) in a screw cap test tube. The pH of the cloudy red mixture was adjusted from 4.00 to 5.70 by the addition of 0.1N NaOH and mixed with a rotary mixer at 4° C. in the dark for 11 hrs. The mixture was centrifuged (2000 RPM×2 mins) and the light red supernate was carefully removed with a pasteur pipet and saved for analysis. The dark red pellet was re-suspended in 10.0 ml of water, briefly stirred, centrifuged and the supernate saved for analysis. This was repeated five times. After the last wash, the AD-HSA/MS-U were dehydrated with acetone and allowed to air dry. The MS product was a dark red powder 11.6 mg, 97% yield, containing 18 wt % AD.

In Vitro AD Release: Dynamic Column Elution Method

A dynamic flow column was used to measure in vitro drug release: 2.0 ml of water was added to the dry AD-HSA/MS-U (11.61 mg), the resulting red slurry was pipeted into a 140 mm×7 mm glass column. The ends of the column were modified with chromatography caps packed with glass wool and attached to threaded zero-volume collectors that were connected to 1.0 mm I.D. Teflon tubing. Care was taken to ensure that all the AD-HSA/MS-U were transferred into the column. The column was then placed in a circulating water bath at 37° C. Physiological saline was pumped through the column at 0.4 ml/min with an HPLC pump (ALTEX model 110A). Fractions were collected every 30 mins for 15 hrs at 4° C. Wash in each fraction was analyzed at 480 nm by UV/VIS to determine the AD concentration eluted from the AD/HSA/MS-U. All subsequent dynamic flow in vitro release studies were performed as just described unless otherwise noted. See Table 8.

TABLE 8

| AD Release From 18 wt % AD-HSA/MS-U (29 $\mu$m) 11.61 mg AD-HSA/MS-U (2.09 mg AD) | | | | | | | |
|---|---|---|---|---|---|---|---|
| | Time (hrs) | | | | | | |
| Drug Release | 2.0 | 4.0 | 6.0 | 8.0 | 10.0 | 12.0 | 14.0 |
| Wt AD (mg) | 0.40 | 0.09 | 0.03 | 0.01 | 0.01 | 0.0 | 0.0 |
| Cumulative Wt AD (mg) | 0.40 | 0.49 | 0.52 | 0.53 | 0.54 | 0.54 | 0.54 |
| % Released | 19 | 24 | 25 | 25 | 26 | 26 | 26 |

EXAMPLE 26

33 wt % Adriamycin-Polyglutamic Acid (12%)-Human-Serum Albumin/Microspheres-Unquenched A volume of 5.0 ml of the stock AD solution (10.46 mg AD) prepared in Example 28 was combined with 11.39 mg of PGA (12%)-HSA/MS-U (synthesized in Example 19) in a screw cap test tube. The pH of the cloudy red mixture was adjusted from 4.45 to 5.84 by the addition of 0.1N NaOH and mixed with a rotary mixer at 4° C. in the dark for 11 hrs. The AD-PGA (12%)-HSA/MS-U were removed from the drug free solution and the bound concentration of AD was determined as described above. The product was a dark red powder, 15.6 mg, 91% yield. Concentration of the bound AD to PGA (12%)-HSA/MS-U was 5.57 mg or 33 wt %.

In Vitro Release

The in vitro release of the free AD from AD-PGA 2%)/MS-U (15.6 mg) was measured and the results set forth in Table 9.

TABLE 9

AD Release from 33 wt % AD-PGA(11%)-HSA/MS-U (34 μm)
15.62 mg AD-PGA(11%)-HSA/MS-U (5.15 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 1.11 | 0.41 | 0.16 | 0.08 | 0.08 | 0.07 | 0.05 |
| Cumulative Wt AD (mg) | 1.11 | 1.52 | 1.68 | 1.76 | 1.84 | 1.91 | 1.96 |
| % Released | 22 | 30 | 33 | 34 | 36 | 37 | 38 |

EXAMPLE 27

39 wt % Adriamycin-Polyglutamic Acid (16%)-Human Serum Albumin/Microspheres-Unquenched

A volume of 5.0 ml of the stock AD solution (10.46 mg AD) prepared in Example 25 was combined with 10.40 mg of PGA (16%)-HSA/MS-U (synthesized in Example 19) in a screw cap test tube. The pH of the cloudy red mixture was adjusted from 4.32 to 5.80 by the addition of 0.1N NaOH and mixed with a rotary mixer in the dark at 4° C. for 11 hrs. AD-PGA(16%)-HSA/MS-U were washed out of the free drug solution, and concentration of the bound AD was determined as described above. The product was a dark red powder, 11.1 mg, 65% yield. Concentration of the bound AD was 6.70 mg or 39 wt %.

In vitro Release

The in vitro release results of free AD from AD-PGA(16%)-HSA/MS-U (11.1 mg) are set forth in Table 10.

TABLE 10

AD Release From 39 wt % AD-PGA(16%)-HSA/MS-U (29 μm)
11.08 mg AD-PGA(16%)-HSA/MS-U (4.33 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.85 | 0.29 | 0.19 | 0.14 | 0.12 | 0.11 | 0.09 |
| Cumulative Wt AD (mg) | 0.85 | 1.14 | 1.33 | 1.47 | 1.59 | 1.70 | 1.79 |
| % Released | 20 | 26 | 31 | 34 | 37 | 39 | 41 |

EXAMPLE 28

46 wt % Adriamycin-Polyglutamic Acid(22%)-Human Serum Albumin/Microspheres-Unquenched

A volume consisting of 5.0 ml of the stock AD solution (10.46 mg AD) prepared in Example 25 was combined with 10.1 mg of PGA(22%)-HSA/MS-U (synthesized in Example 19) in a screw cap test tube. The pH of the cloudy red mixture was adjusted from 4.43 to 5.80 by the addition of 0.1N NaOH and mixed with a rotary mixer in the dark at 4 C for 11 hrs. AD-PGA(22%)-HSA/MS-U were washed out of the free drug solution, dehydrated and concentration of the bound AD was determined as described above. The product was a dark red powder 14.7 mg, 78% yield. Concentration of the bound AD was 8.61 mg or 46 wt %.

In Vitro Release

The release of the free AD from the AD-PGA(22%)-HSA/MS-U (14.7 mg) produced in this procedure was measured and the results set forth in Table 11.

TABLE 11

AD Release from 46 wt % AD-PGA(22%-HSA/MS-U (29 μm)
8.41 mg AD-PGA(22%)-HSA/MS-U (3.86 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 1.01 | 0.24 | 0.26 | 0.14 | 0.11 | 0.08 | 0.07 |
| Cumulative Wt AD (mg) | 1.01 | 1.25 | 1.51 | 1.65 | 1.76 | 1.84 | 1.91 |
| % Released | 26 | 32 | 39 | 43 | 16 | 48 | 50 |

EXAMPLE 29

18 wt % Adriamycin-Human Serum Albumin/Microspheres-Quenched

AD (50.5 mg), was dissolved in 25.0 ml of water in a volumetric flask. A volume consisting of 5.0 ml of the clear dark red solution (10.1 mg AD) was combined with 10.7 mg of HSA/MS-Q (Example 18) in a screw cap test tube. The pH of the cloudy red mixture was adjusted from 2.99 to 5.83 by the addition of 0.1N NaOH and mixed with a rotary mixer at 4° C. in the dark for 11 hrs. AD-HSA/MS-Q were removed from the free AD solution, washed, and dehydrated as described in Example 28. The wash was saved for analysis. The product was dark red powder, 7.1 mg, 54% yield.

In Vitro Release

The release of free AD from the AD-HSA/MS-Q (7.1 mg) produced in this procedure was measured and the results set forth in Table 12.

TABLE 12

AD Release from 18 wt % AD-HSA/MS-Q (26 μm)
7.08 mg AD-HSA/MS-Q (1.28 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.68 | 0.21 | 0.12 | 0.06 | 0.03 | 0.03 | 0.01 |
| Cumulative Wt AD (mg) | 0.68 | 0.89 | 1.01 | 1.07 | 1.10 | 1.13 | 1.14 |
| % Released | 53 | 70 | 77 | 82 | 85 | 87 | 88 |

EXAMPLE 30

21 wt% Adriamycin-Polyglutamic Acid (11%)-Human Serum Albumin/Microspheres-Quenched

A volume consisting of 5.0 ml of the stock AD solution (10.1 mg AD) prepared as above was combined with 11.0 mg of PGA (11%)-HSA/MS-Q (synthesized in Example 20) in a screw cap test tube. The pH of the cloudy red mixture was adjusted from 3.46 to 5.81 by the addition of 0.1N NaOH and mixed with a rotary mixer at 4° C. in the dark for 11 hrs. AD-PGA (11%)-HSA/MS-Q were washed out of the free AD solution, dehydrated and concentration of the bound drug was determined as above. The product was a dark red powder, 10.88 mg, 82% yield. Concentration of the bound AD was 2.83 mg or 21 wt %.

In vitro Release

The release of the free AD from the AD-PGA(11%)-HSA/MS-Q (10.9 mg) was measured and the results set forth in Table 13.

TABLE 13

AD Release from 21 wt % AD-PGA (11%)-HSA/MS-Q (23 μm)
10.88 mg AD-PGA (11%)-HSA/MS-Q (2.23 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 1.30 | 0.21 | 0.10 | 0.04 | 0.01 | 0.02 | 0.01 |
| Cumulative Wt AD (mg) | 1.29 | 1.50 | 1.60 | 1.64 | 1.65 | 1.67 | 1.68 |
| % Released | 58 | 67 | 72 | 73 | 74 | 75 | 75 |

EXAMPLE 31

25 wt% Adriamycin-Polyglutamic Acid (15%)-Human Serum Albumin/Microspheres-Quenched A volume consisting of 5.0 ml of the stock AD solution (10.1 mg AD) prepared as above was combined with 9.9 mg of PGA (15%)-HSA/MS-Q (synthesized in Example 20) in a screw cap test tube. The pH of the cloudy red mixture was adjusted from 3.59 to 5.84 by the addition of 0.1N NaOH and mixed with a rotary mixer at 4° C. in the dark for 11 hrs. AD-PGA(15%)-HSA/MS-Q were washed out of the free AD solution, dehydrated and concentration of the bound drug was determined as described above. The product was dark red powder, 5.7 mg, 43% yield. Concentration of the bound AD was 3.33 mg or 25 wt %.

In vitro Release

The release of the free AD from the AD-PGA(15%)-HSA/MS-Q (5.7 mg) was measured and the results set forth in Table 14.

TABLE 14

AD Release from 25 wt % AD-PGA (15%)-HSA/MS-Q (28 μm)
5.70 mg AD-PGA (15%)-HSA/MS-Q (1.43 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.77 | 0.08 | 0.02 | 0.02 | 0.02 | 0.02 | 0.01 |
| Cumulative Wt AD (mg) | 0.77 | 0.85 | 0.87 | 0.89 | 0.91 | 0.93 | 0.94 |
| % Released | 54 | 59 | 61 | 62 | 64 | 65 | 66 |

EXAMPLE 32

33 wt % Adriamycin-Polyglutamic Acid (19%)-Human Serum Albumin/Microspheres-Quenched A volume consisting of 5.0 ml of the stock adriamycin solution (10.1 mg AD) prepared as above was combined with 10.1 mg of PGA (19%)-HSA/MS-Q (synthesized in Example 20) in a screw cap test tube. The pH of the cloudy red mixture was adjusted from 3.71 to 5.84 by the addition of 0.1N NaOH and mixed with a rotary mixer at 4° C. in the dark for 11 hrs. AD-PGA (19%)-HSA/MS-Q were washed out of the free AD solution, dehydrated and concentration of the bound drug was determined as described above. The product was a dark red powder, 7.9 mg, 53% yield. Concentration of the bound drug was 4.9 mg or 33 wt %.

In vitro Release

The release of the free AD from the AD-PGA (19%)-HSA/MS-Q (7.9 mg) was measured and the results set forth in Table 15.

TABLE 15

AD Release from 33 wt % AD-PGA (19%)-HSA/MS-Q (24 μm)
7.88 mg AD-PGA (19%)-HSA/MS-Q (2.58 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.77 | 0.20 | 0.14 | 0.09 | 0.08 | 0.07 | 0.07 |
| Cumulative Wt AD (mg) | 0.77 | 0.97 | 1.11 | 1.20 | 1.28 | 1.35 | 1.42 |
| % Total AD | 30 | 38 | 43 | 47 | 50 | 52 | 55 |

EXAMPLE 33

Ion Exchange Release Properties of Adriamycin-Albumin/Microspheres-Quenched

AD was bound to (1) HSA/MS-Q (quenched with 2-aminoethanol), (2) HSA-MS-Q (quenched with glycine) and (3) PGA (15%)-HSA/MS-Q according to the procedure described above. MS were washed out of the free drug solution, dehydrated and concentration of the bound AD was determined as described above. After dehydration, the AD-MS had a yield of (1) 8.28 mg, 75%, (2) 7.98 mg, 77% and (3) 9.50 mg, 57%. Concentration of the bound drug for each sample was (1) 1.4 mg or 14%, (2) 1.6 mg or 20% and (3) 4.8 mg or 28%.

In vitro Release

The AD-albumin/MS samples were separately loaded in the release column as described above. Water was used as the mobile phase for the first 5.0 hrs, then exchanged for physiological saline for the remainder of the experiment. Release data is set forth in Tables 16, 17 and 18.

TABLE 16

AD Release from 14 wt % AD-HSA/MS-Q (aminoethanol)
(25 μm) 8.28 mg AD-HSA/MS-Q (1.16 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.16 | 0.12 | 0.17 | 0.30 | 0.05 | 0.02 | 0.0 |
| Cumulative Wt AD (mg) | 0.16 | 0.28 | 0.45 | 0.75 | 0.80 | 0.82 | 0.82 |
| % Released | 14 | 24 | 39 | 65 | 69 | 71 | 71 |

TABLE 17

AD Release from 20 wt % AD-HSA/MS-Q (glycine) (25 μm)
7.98 mg AD-HSA/MS-Q (1.60 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.14 | 0.12 | 0.38 | 0.18 | 0.08 | 0.08 | 0.08 |
| Cumulative Wt AD (mg) | 0.14 | 0.26 | 0.64 | 0.82 | 0.90 | 0.98 | 1.06 |
| % Released | 9 | 16 | 40 | 52 | 56 | 61 | 66 |

TABLE 18

AD Release from 28 wt % AD-PGA (15%)-HSA/MS-Q (28 μm)
9.54 mg AD-PGA (15%)-HSA/MS-Q (2.67 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt AD (mg) | 0.08 | 0.03 | 0.23 | 0.79 | 0.25 | 0.13 | 0.12 |
| Cumulative Wt AD (mg) | 0.08 | 0.11 | 0.34 | 0.13 | 1.38 | 1.51 | 1.63 |

TABLE 18-continued

AD Release from 28 wt % AD-PGA (15%)-HSA/MS-Q (28 μm)
9.54 mg AD-PGA (15%)-HSA/MS-Q (2.67 mg AD)

| Drug Release | Time (hrs) | | | | | | |
|---|---|---|---|---|---|---|---|
| | 2.0 | 4.0 | 6.0 | 8.0 | 10.0 | 12.0 | 14.0 |
| % Released | 3 | 4 | 13 | 42 | 52 | 57 | 61 |

EXAMPLE 34

In vitro Release of Adriamycin from Albumin/Microspheres in a Static System

PGA(10%)-HSA/MS-Q containing AD, synthesized as described above were washed out of the free AD solution, dehydrated and concentration of the bound AD was determined as described above. The product was a dark red powder, 6.1 mg, 75% yield. The concentration of the bound drug was 2.6 mg or 31.7 wt %.

In vitro Release

The AD-PGA(10%)-HSA/MS (6.1 mg) were combined with 2.0 ml of physiological saline in a screw cap test tube and placed in a 37° C. shaker water bath. Every 30 mins, the cloudy red mixture was centrifuged and 50 μl was removed from the clear red supernate, diluted in 5.0 ml of physiological saline. The concentration of the released AD was then determined as previously described above. This procedure was repeated until the amount of release drug remained constant (i.e., no more AD released). The AD-PGA(10%)-HSA/MS-Q were then washed (5X) with 10.0 ml volumes of water to remove all free AD. After the last water wash was decanted, the MS were re-suspended with 2.0 ml of saline and the process duplicated for the remainder of the experiment (15 hrs.)

EXAMPLE 35

In Vivo Studies

Toxicity of Adriamycin-Polyglutamic Acid (15%)-Human Serum Albumin/Microspheres-Quenched in CD-1 Mice AD-PGA(15%)-HSA/MS-Q were synthesized according to the procedure described above. The product was a dark red powder with 27 wt % bound AD and total yield of 76%. MS had a size range of 20–40 μm.

CD-1 white female mice, 5–7 weeks of age, weighing 30–33 g were injected by the intraperitoneal (i.p.) route with AD at concentrations of 0.6 mg and 1.5 mg dissolved in 0.5 ml of sterile saline. A second group of animals were injected with AD-PGA(15%)-HSA/MS-Q with 0.6, 1.5, and 2.5 mg of bound AD. For each concentration of the free and bound drug, 5 mice were used. PGA(15%)-HSA/MS-Q without AD was used for a control group and injected in equivalent weight amounts. Animals were then observed over a two-month period and fatalities were recorded for each group and tabulated. See Table 19.

TABLE 19

Toxicity of AD-PGA-HSA/MS-U in CD-1 Mice by i.p. Injection

| Preparation and dose | Survival from Time of Administration | | | | |
|---|---|---|---|---|---|
| | 7 days | 14 days | 21 days | 28 days | 35 days |
| AD (0.6 mg) | 5/5 | 1/5 | 1/5 | 1/5 | 1/5 |
| AD (1.5 mg) | 5/5 | 0/5 | — | — | — |
| AD-PGA-HSA/MS (AD 0.6 mg) | 5/5 | 5/5 | 5/5 | 5/5 | 5/5 |

TABLE 19-continued

Toxicity of AD-PGA-HSA/MS-U in CD-1 Mice by i.p. Injection

| Preparation and dose | Survival from Time of Administration | | | | |
|---|---|---|---|---|---|
| | 7 days | 14 days | 21 days | 28 days | 35 days |
| (2.22 mg MS) AD-PGA-HSA/MS (AD 1.5 mg) (4.44 mg MS) | 5/5 | 5/5 | 5/5 | 5/5 | 5/2 |
| AD-PGA-HSA/MS (AD 2.5 mg) (9.26 mg MS) | 5/5 | 4/5 | 1/5 | 0/5 | — |
| PGA-HSA/MS (2.22 mg MS) | 5/5 | 5/5 | 5/5 | 5/5 | 5/5 |
| PGA-HSA/MS (4.44 mg MS) | 5/5 | 5/5 | 5/5 | 5/5 | 5/5 |
| PGA-HSA/MS (9.26 mg MS) | 5/5 | 5/5 | 5/5 | 5/5 | 5/5 |

EXAMPLE 36

HSA/MS were readily prepared as described above containing up to 18 wt % of the anti-tumor drug adriamycin (AD). The binding of AD to HSA/MS involved two mechanisms; (1) the covalent attachment of the primary amine associated with AD to free reactive mono-dialdehydes on HS/MS-unquenched (U) and (2) physical binding of AD to HSA/MS-quenched (Q).

Terry, R.N., M.S., Thesis, University of Florida (1980) demonstrated that PGA readily formed stoichiometric ionic salts with basic drugs such as AD. This is due to interactions between the anionic carboxyl groups associated with PGA and the cationic primary amine group located on the daunosamine ring of AD. Terry also found that by subjecting the PGA-AD complex to an appropriate electrolyte, the ionic salt would dissociate and release the AD. The addition of PGA to the HSA/MS made possible the preparation of AD-PGA-HSA/MS containing up to 45% of the drug through the formation of this AD-salt complex. This is demonstrated in the comparison of the binding data for AD in Table 20 for (HSA/MS-U and PGA-HSA/MS-U and Table 21 for (HSA/MS-Q and PGA-HSA/MS-Q).

TABLE 20

Amount of Bound AD for Unquenched HSA/MS and PGA-HSA/MS

| Wt % of Added PGA | Wt % of Bound AD |
|---|---|
| 0 | 18 |
| 12 | 33 |
| 16 | 39 |
| 22 | 46 |

TABLE 21

Amount of Bound AD for Quenched HSA/MS and PGA-HSA/MS

| Wt % of Added PGA | Wt % of Bound AD |
|---|---|
| 0 | 18 |
| 11 | 21 |
| 15 | 25 |
| 19 | 33 |

The data shows that as the concentration of PGA increases in the MS, the wt % of bound AD also increases. This data also shows that the amount of bound AD is higher for the MS-U than the MS-Q at comparable amounts of PGA and is attributable to the increased amount of AD that can be covalently bound to have HSA/MS-U than the physically bound AD to HSA/MS-Q.

The ionic AD-salt complex is sensitive to pH. Adjusting the pH directly affected the amount of AD bound to the PGA-HSA/MS-Q. The optimum pH for binding was found to be 6.0 and corresponded to 32 wt % complexed drug.

AD-HSA/MS were mounted in epoxy and serial section with a ultramicrotome, the sections were mounted on TEM grids and examined with an optical microscope. The red chromophor of AD could be seen throughout the slices and indicated that the drug had penetrated into the matrix of the HSA/MS as well as on the surface.

It is a feature of the invention that the hydrophilic nature of HSA/MS allows for the incorporation of therapeutic agents to the albumin/MS after their synthesis. This is inherently different from prior art procedures which add the drugs to the aqueous phase before the dispersion process and the formation of the microspheres. The advantage of drug addition after MS synthesis are: (1) higher drug loadings and (2) ability to bind chemically sensitive drugs that otherwise may be affected during the formation of the MS.

The in vitro AD release rates for the AD-albumin/MS were found to be readily controlled and due to the three distinct binding mechanisms of AD to albumin/MS; (1) slow-hydrolytic degradation of covalent bonds, (2) medium-dissociation of the drug salt complex, and (3) fast-release of physically adsorbed drug.

For the unquenched MS (HSA/MS-U and PGA-HSA/MS-U) the amount of AD released in 15 hrs varied from 23% to 50%. Increasing the concentration of PGA in HSA/MS increased the amount of released AD. Since the PGA-AD salt complex dissociates faster than hydrolytic degradation of covalently bound AD, increasing the amount of incorporated PGA increases the rate of AD release. For AD-HSA/MS-Q and AD-PGA/MS-Q, the amount of AD released in 15 hrs varied from 55% to over 80%. As the amount of PGA increases, the percent of the total amount of AD that is released decreases. Since the MS are quenched, the number of reactive aldehydes that are available to covalently bind AD are reduced. The predominate drug binding mechanism would then be by physical association and drug-salt formation. The physically adsorbed AD is released faster than salt dissociation. Therefore, as the amount of the PGA is increased in the MS, a higher percentage of the bound AD is associated with the salt complex. This causes a larger % of the released AD to be by salt dissociation which reduces the release rate. With respect to quenching, glycine would incorporate a higher amount of terminal carboxyl groups than the amino alcohol due to basic structural differences between the two molecules. Higher amounts of free carboxyl groups would allow higher concentrations of AD bound by salt formation. Because the salt complex is stable in water, the MS with the highest concentration of carboxyl groups (AD-PGA-HSA/MS-Q, COOH) would release the lowest amount of AD when water was used as the mobile phase through the dynamic flow column. AD-HSA/MS-Q ,(OH), would contain the least amount of carboxyl groups (albumin itself contains some of these groups) and therefore would release the highest amount of AD during the water phase. When the mobile phase is exchanged with saline, the salt dissociates releasing AD.

Dynamic flow in vitro release rates do not accurately represent kinetic behavior in vivo, only animal models can determine that type of information. It does, however, allow comparisons to be made between drug carriers so that adequate evaluations can be made before expensive laboratory animal models are used. Furthermore, the dynamic column system is, at best, a representation of controlled drug delivery in the blood circulatory system due to the fast continuous flow. In actuality, MS implanted inside a solid tumor would not be subject to such a rapid turnover of fluid. The slow fluid turnover in the tumor can be better represented by a semi-static in vitro release model. In a static system, drug release from AD-HSA/MS would be regulated by the mechanisms described as well as the concentration of released AD in the AD-HSA/MS environment. As the drug is released into the closed system (i.e., tumor mass), a concentration level would be reached where further drug release would be inhibited. Drug seepage out of the tumor area would then reduce the concentration gradient to a point where more drug would then be released from AD-HSA/MS.

In the toxicity study reported above, a dose level of 600 $\mu$g of free AD killed over 80% of the animals tested. The same amount of AD now bound to PGA-HSA/MS resulted in no deaths. When AD-PGA-HSA/MS with 1500 g of bound AD were administered i.p., 60% of the mice survived. Another hazard with AD is the severe necrotic lesions that develop at the site of injection when there is drug leakage around the needle. These ulcers can take months to heal. All animals treated with free AD developed these ulcers. No ulcer development was seen with animals injected with the AD containing MS. Control groups consisting of PGA-HSA/MS did not demonstrate any noticeable toxic effects.

An important characteristic of a successful drug implant is the ability of the drug-carrier to biodegrade once implanted and release of the therapeutic agent. Albumin/MS synthesized in this study were examined for these properties. It was found that highly cross-linked FTIC-BSA/MS that were injected into CD-1 mouse muscle tissue started to degrade by the fourth week and remained immobilized at the site of injection. By varying the cross-linking density, variations in the rate of degradation in vivo may be achieved.

AD-HSA/MS were also implanted into CD-1 muscle tissue and examined after tissue removal. The AD molecule has natural fluorescent abilities and could be easily observed with the optical microscope under fluorescent light. Tissue samples observed after four weeks from day of injection still showed the red chromophor of AD in the surrounding tissue next to the immobilized AD-HSA/MS.

This study demonstrates three important characteristics of the albumin/MS produced according to the invention. These are: (1) to remain localized at site of injection, (2) biodegradation after implantation and (3) drug releasing properties after injection.

Preparation of Bleomycin-Albumin/Microspheres

EXAMPLE 37

Bleomycin Sulfate (BLM) was supplied in 10.0 ml sealed glass vials containing between 8 and 9 mg of a lyophilized white powder that was amorphous in texture. To measure the exact concentration of the BLM, the glass vials were opened in the exhaust hood and the drug dissolved by the addition of known volumes of water. The concentration was then determined with the UV/VIS at an adsorbance of 294 nm and using an extinction coefficient of 12.15 ml/mg (Windholz, M., et al, *The Merck Index,* Merck & Co., Inc. p. 171 (1976)).

EXAMPLE 38

30 wt % Bleomycin-Human Serum Albumin/Microspheres-Unquenched

A stock solution of BLM was prepared containing 66.7 mg BLM in 25.0 ml of water. An aliquot consisting of 5.0 ml of the clear solution (13.3 mg BLM) was combined with 11.3 mg HSA/MS-U (synthesized as described in Example 1) in a screw cap test tube. The pH of the Brown cloudy mixture was adjusted from 4.23 to 5.97 by the addition of 0.1N NaOH and mixed with a rotary mixer in the dark at 4° C. for 7 hrs. BLM-HSA/MS-U were washed free of the unbound BLM and supernate saved for analysis as described above. After the last wash, the MS were dehydrated with acetone and allowed to air dry. The MS product was a brown powder, 11.7 mg, 73% yield containing 30 wt % drug.

In vitro Release

The release of free BLM from BLM/HSA/MS-U (11.7 mg) was performed using the in vitro dynamic flow column described above. See Table 22.

TABLE 22

BLM Release from 29 wt % BLM-HSA/MS-U (29 μm)
11.67 mg BLM-HSA/MS-U (3.50 mg BLM)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 1.29 | 0.06 | 0.04 | 0.03 | 0.02 | 0.02 | 0.01 |
| Cumulative Wt BLM (mg) | 1.29 | 1.35 | 1.39 | 1.42 | 1.44 | 1.46 | 1.47 |
| % Released | 37 | 39 | 40 | 41 | 41 | 42 | 42 |

EXAMPLE 39

31 wt % Bleomycin-Polyglutamic Acid (9%)-Human Serum Albumin/Microspheres-Unquenched An aliquot consisting of 5.0 ml of the BLM stock solution (13.34 mg BLM) prepared as described above was combined with 12.7 mg of PGA (9%)-HSA/MS-U (synthesized as described above) in a screw cap test tube. The pH of the mixture was adjusted from 4.71 to 6.00 by the addition of 0.1N NaOH and mixed at 4° C. in the dark for 7 hrs. The BLM-PGA(9%)-HSA/MS-U were removed from solution and concentration of the bound drug was determined as described above. The product was a brown powder, 13.15 mg, 72% yield. Concentration of the bound drug was 5.69 mg or 31 wt %.

In vitro Release

The in vitro release of free BLM from BLM-PGA-(9%)-HSA/MS-U (13.15 mg) was measured as described above. See Table 23.

TABLE 23

BLM Release from 31 wt % BLM-PGA (9%)-HSA/MS-U (27 μm)
13.15 mg BLM-PGA (9%)-HSA/MS-U (4.08 mg BLM)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 2.32 | 0.09 | 0.06 | 0.03 | 0.04 | 0.02 | 0.0 |
| Cumulative | 2.32 | 2.41 | 2.47 | 2.50 | 2.54 | 2.56 | 2.56 |
| Wt BLM (mg) | | | | | | | |
| % Released | 57 | 59 | 61 | 61 | 62 | 63 | 63 |

EXAMPLE 40

30 wt % Bleomycin-Polyglutamic Acid (14%)-Human Serum Albumin/Microspheres-Unquenched An aliquot consisting of 5.0 ml of the stock BLM solution (13.34 mg BLM) prepared as above was combined with 12.8 mg of PGA(14%)-HSA/MS-U (synthesized as described above) in a screw cap test tube. The pH of the cloudy mixture was adjusted from 4.83 to 6.00 by the addition of 0.1N NaOH and mixed with a rotary mixer at 4° C. in the dark for 7 hrs. BLM-PGA(14%)-HSA/MS-U were washed out of the free drug solution, dehydrated and concentration of the bound drug was determined as described in Example 38. The product was a brown powder, 13.8 mg, 75% yield. Concentration of the bound BLM was 5.56 mg or 30 wt %.

In vitro Release

The in vitro release of the free BLM from BLM-PGA(14%)-HSA/MS-U (13.8 mg) was measured as described above. See Table 24.

TABLE 24

BLM Release from 30 wt % BLM-PGA (14%)-HSA/MS-U (31 μm)
13.8 mg BLM-PGA (14%)-HSA/MS-U (4.14 mg BLM)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 2.41 | 0.06 | 0.03 | 0.02 | 0.02 | 0.01 | 0.01 |
| Cumulative Wt BLM (mg) | 2.41 | 2.47 | 2.50 | 2.52 | 2.54 | 2.55 | 2.56 |
| % Released | 58 | 60 | 60 | 61 | 61 | 62 | 62 |

EXAMPLE 41

23 wt % Bleomycin-Human Serum Albumin/Microspheres-Quenched

A stock solution of BLM was prepared containing 62.7 mg dissolved with 25.0 ml of water in a volumetric flask. An aliquot consisting of 5.0 ml (12.54 mg) was combined with 11.9 mg of HSA/MS-Q in a screw cap test tube. The pH of the mixture was adjusted from 3.95 to 5.95 by the addition of 1.0N NaOH and mixed with a rotary mixer at 4° C. in the dark for 19 hrs. The BLM-HSA/MS-Q were removed from solution, dehydrated and concentration of bound drug was determined as described above. The product was a brown powder, 11.8 mg, 76% yield. Concentration of the bound drug was 3.58 or 23 wt %.

In vitro Release

The in vitro release of the free BLM from BLM-HSA/MS-Q (11.81 mg) was measured and the results set forth in Table 25.

TABLE 25

BLM Release from 23 wt % BLM-HSA/MS-Q (29 μm)
11.81 mg BLM-HSA/MS-Q (2.71 mg)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 1.16 | 0.04 | 0.02 | 0.02 | 0.01 | 0.0 | 0.0 |
| Cumulative Wt BLM (mg) | 1.16 | 1.20 | 1.22 | 1.24 | 1.25 | 1.25 | 1.25 |
| % Released | 43 | 44 | 45 | 46 | 46 | 46 | 46 |

EXAMPLE 42

20 wt % Bleomycin-Polyglutamic Acid(9%)-Human Serum Albumin/Microspheres-Quenched An aliquot consisting of 5.0 ml of the stock BLM solution (12.54 mg BLM) was combined with 13.9 mg of PGA(9%)-HSA/MS-Q in a screw cap test tube. The pH of the mixture was adjusted from 3.68 to 5.98 by the addition of 0.1N NaOH and mixed with a rotary mixer at 4° C. in the dark for 19 hrs. The BLM-PGA(9%)-HSA/MS were washed out of the free BLM solution, dehydrated and concentrations of the bound drug was determined as described above. The product was a brown powder, 16.2 mg, 84% yield. Concentration of the bound drug was 5.51 mg or 28 wt %.

In vitro Release

The release of the free BLM from BLM-PGA(9%)-HSA/MS-Q (16.20 mg) was measured and the results are set forth in Table 26.

TABLE 26

BLM Release from 28 wt % BLM-PGA (9%)-HSA/MS-Q (27 μm)
16.20 mg BLM-PGA (9%)-HSA/MS-Q (4.54 mg BLM)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 2.53 | 0.05 | 0.02 | 0.01 | 0.01 | 0.0 | 0.0 |
| Cumulative Wt BLM (mg) | 2.53 | 2.58 | 2.60 | 2.61 | 2.62 | 2.62 | 2.62 |
| % Released | 56 | 57 | 57 | 57 | 58 | 58 | 58 |

EXAMPLE 43

29 wt % Bleomycin-Polyglutamic Acid (14%)-Human Serum Albumin/Microspheres-Quenched An aliquot consisting of 5.0 ml of the stock BLM solution (12.54 mg BLM) was combined with 12.1 mg of PGA(14%)-HSA/MS-Q in a screw cap test tube. The pH of the mixture was adjusted from 3.65 to 5.97 by the addition of 0.1N NaOH and mixed with a rotary mixer at 4° C. in the dark for 19 hrs. The BLM-PGA(14%)-HSA/MS-Q were washed out of the free BLM solution, dehydrated and concentration of the bound drug was determined as described bove. The product was a brown powder, 13.2 mg, 78% yield. Concentration of the bound drug was 4.98 or 29 wt %.

In vitro Release

The release of the free BLM from BLM-PGA(14%)-HSA/MS-Q (13.21 mg) was measured and release results are set forth in Table 27.

TABLE 27

BLM Release from 29 wt % BLM-PGA (14%)-HSA/MS-Q (31 μm)
13.21 mg BLM-PGA (14%)-HSA/MS-Q (3.83 mg BLM

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt BLM (mg) | 2.15 | 0.04 | 0.02 | 0.01 | 0.0 | 0.0 | 0.0 |
| Cumulative Wt BLM (mg) | 2.15 | 2.19 | 2.21 | 2.22 | 2.22 | 2.22 | 2.22 |
| % Released | 56 | 57 | 58 | 58 | 58 | 58 | 58 |

EXAMPLE 44

12 wt % Gentamycin-Human Serum Albumin/Microspheres-Unquenched

A solution of GMC (gentamycin sulfate) was prepared containing 257.9 mg dissolved with 25.0 ml of water in volumetric flask. An aliquot consisting of 5.0 ml of the clear solution (51.58 mg) was combined with 50.5 mg of the dehydrated HSA/MS-U (synthesized as described in Example 1 in a screw cap test tube. The pH of the brown cloudy mixture was adjusted from 5.18 to 5.70 by the addition of 0.1N NaOH and mixed at 4° C. in the dark for 12 hrs. GMC-HSA/MS-U were washed free of the unbound GMC and supernate saved for analysis as described above. After the last wash, the MS were dehydrated with acetone and allowed to air dry. The MS product was a brown powder, 52.4 mg, 92% yield containing 12 wt % drug.

Gentamycin sulfate (GMC) has an aminoglycoside structure with no detectable absorbance in either the ultraviolet or visable range. In order to quantitate the concentration of GMC for the drug binding experiments, a modification of the Barends et al [A. J. Chromatography, Vol. 222, pg. 316 (1981)] procedure was used.

EXAMPLE 45

16 wt % Gentamycin-Polyglutamic Acid(17%)-Human Serum Albumin/Microspheres-Unquenched A solution of GMC was prepared containing 252.02 mg dissolved in 25.0 ml of water in a volumetric flask. An aliquot consisting of 10.0 ml of the clear solution (100.81 mg) was combined with 119.06 mg of PGA(17%)-HSA/MS-U in a screw cap test tube. The pH of the brown cloudy mixture was adjusted from 5.30 to 5.74 by the addition of 0.1N NaOH and mixed with a rotary mixer at 4° C. in the dark for 12 hrs. GMC-PGA(17%)-HSA/MS-U were removed from the free drug solution by centrifugation, washed and dehydrated as described above. The supernate was saved for analysis. The MS product was a brown powder, 113.6 mg, 81% yield.

EXAMPLE 46

15 wt % Gentamycin-Polyglutamic Acid(19%)-Bovine Serum Albumin/Microspheres-Unquenched A solution of GMC was prepared containing 252.94 mg dissolved in 25.0 ml of water in a volumetric flask. An aliquot consisting of 10.0 ml of the clear solution (101.18 mg GMC) was combined with 127.72 mg of the dehydrated PGA(19%)-BSA/MS-U in a screw cap test tube. The pH of the brown cloudy mixture was adjusted from 5.12 to 5.83 by the addition of 0.1N NaOH and mixed with a rotary mixer at 4° C. in the dark for 12 hrs. GMC-PGA(19%)-BSA/MS-U were removed from the free drug solution by centrifugation washed and dehydrated as described above.

In vitro Release

The in vitro release of GMC from GMC-PGA(19%)-BSA/MS-U was performed as described above. Concentration of the free drug in the collected fractions was analyzed as described in Example 44. Release data is set forth in Table 28.

TABLE 28

GMC Release from 18 wt % GMC-PGA (19%)-BSA/MS-U (18 μm)
16.37 mg GMC-PGA (19%)-BSA/MS-U (246 gm GMC)

| Drug Release | Time (hrs) | | | | | | |
|---|---|---|---|---|---|---|---|
| | 2.0 | 4.0 | 6.0 | 8.0 | 10.0 | 12.0 | 14.0 |
| Wt GMC (mg) | 1.66 | 0.40 | 0.16 | 0.01 | 0.0 | 0.0 | 0.0 |
| Cumulative Wt GMC (mg) | 1.66 | 2.15 | 2.31 | 2.32 | 2.32 | 2.32 | 2.32 |
| % Released | 66 | 86 | 94 | 95 | 95 | 95 | 95 |

EXAMPLE 47

18 wt % Streptomycin-Polyglutamic Acid(14%)-Bovine Serum Albumin/Microspheres-Unquenched STM (259.6 mg) was dissolved with 25.0 ml of water, 5.0 ml of the clear solution (51.92 mg STM) was combined with 48.3 mg of PGA(14%)-BSA/MS-U prepared as described in Example 24 in a screw cap test tube. The pH of the cloudy white mixture was adjusted from 4.23 to 5.79 by the addition of 0.1N NaOH and mixed with a rotary mixer at 4° C. in the dark for 18 hrs. The mixture was centrifuged (200 RPM×2 mins) and the clear supernate was removed and saved for analysis. The STM-PGA(14%)-BSA/MS-U were removed from the free drug solution, washed and dehydrated. The MS product was a white powder, 27.5 mg, 47% yield.

Streptomycin sulfate (STM) has no detectable absorbance in either the ultraviolet or visable range. As with GMC, STM has to be modified in order to quantitate the amounts of STM bound STM to the MS. The manitol procedure by Grove and Randall in *Assay Methods of Antibiotics a Laboratory Manual,* Welch, H, and Martin Ibaneze, F, eds. Medical Encyclopedia, Inc., New York, N.Y., p. 34 (1975) was used.

EXAMPLE 48

23 wt % Streptomycin-Polyglutamic Acid(14%)-Bovine Serum Albumin/Microspheres-Quenched A volume of 5.0 ml of the stock STM solution (51.92 mg STM) was combined with 38.8 mg of the PGA(14%)-BSA-PGA/MS-Q prepared as described in Example 22 in a screw cap test tube. The pH of the cloudy white mixture was adjusted from 4.32 to 5.86 by the addition of 0.1N NaOH and mixed with a rotary mixer in the dark for 4° C. for 18 hrs. The STM-PGA(14%)-BSA/MS-Q were removed from the free drug solution and the bound STM was determined as described above. The product was a white powder, 34.8 mg, 70% yield. Concentration of bound STM was 11.28 mg or 23 wt %.

EXAMPLE 49

12 wt % Streptomycin-Polyglutamic Acid(14%)-Bovine Serum Albumin/Microspheres-Quenched and Lyophilized A volume of 5.0 ml of the stock STM solution (51.92 mg STM) was combined with 39.7 mg of lyophilized PGA(14%)-BSA/MS-Q in a screw cap test tube. The pH of the cloudy white mixture was adjusted from 4.47 to 5.80 by the addition of 0.1N NaOH and mixed with a rotary mixer in the dark at 4° C. for 18 hrs. STM-PGA(14%)-HSA/MS-Q were washed out of the free STM solution, and concentration of the bound drug was 5.63 mg or 12 wt %.

EXAMPLE 50

13 wt % Streptomycin-Polyglutamic Acid(14%)-Bovine Serum Albumin/Microspheres-Quenched (Wet)

A volume of 5.0 ml of the stock STM solution (51.92 mg STM) was combined with 3.0 ml of PGA(14%)-BSA/MS-Q (9.7 mg/ml) or 29.4 mg total MS, suspended in 3.0 ml of water, in a screw cap test tube. The combination of the two solutions (STM and MS) produced a final volume of 8.0 ml. The pH of the cloudy white mixture was adjusted from 5.10 to 5.91 by the addition of 0.1N NaOH and mixed with a rotary mixer in the dark at 4° C. for 18 hrs. STM-PGA(14%)-BSA/MS-Q were washed out of the free drug solution, and concentration of the bound drug was 4.39 mg or 13 wt %.

EXAMPLE 51

23 wt % Streptomycin-Carboxymethyldextran(12%)-Bovine Serum Albumin/Microspheres-Quenched STM (255.2 mg) was dissolved in 25.0 ml of water, 5.0 ml of the clear solution (51.04 mg STM) was combined with 58.4 mg of CMD(12%)-BSA/MS-Q in a screw cap test tube. The pH of the cloudy white mixture was adjusted from 3.35 to 5.90 by the addition of 0.1N NaOH and mixed with a rotary mixer at 4° C. in the dark for 18 hrs. MS were washed out of the free drug solution, dehydrated and concentration of the bound STM was determined. The product was a white powder, 60.3 mg, 85% yield. Concentration of the bound drug was 23 wt. %.

The albumin protein and polypeptide microsphere compositions of this invention when loaded with biologically active agents are uniquely valuable for localization and controlled release of such agents, as for example, in localized cancer chemotherapy, local delivery of anti-inflammatory drugs, and for localized concentration of antibiotics. The microsphere compositions of this invention are also useful in adjuvant systems as carriers and active agents in stimulating the immune system. Currently used adjuvants (such as Freund's adjuvant) for immunostimulants and vaccines are often highly irritating, produce undesirable fever or highly inflammatory reactions and are short-lived in activity due to metabolic deterioration. Adjuvant compositions in which microspheres of this invention are utilized, for example by loading with specific antigens (i.e., tumor-specific antigens) or non-specific immune stimulants such as BCG constituents of MDP (myramyl dipeptide) afford the advantages of prolonged activity and greater stability as well as increased efficacy and mimimal toxic side effects.

Macrophage are the active cellular agents of the immune defense system of animals and humans and digest or destroy foreign cells or substances and dead cellular material. In some diseases, macrophage and other cells are invaded but do not attack the viral or parasitic invaders. Suprisingly, the microspheres of this invention have been found to be readily ingested by macrophage by phagocytic uptake. Consequently they are uniquely suitable as carriers for bioactive agents which can attack the dormal viral or parasitic cells or can activate microphage. They are, therefore, especially useful as macrophage activation compositions and for treatment of diseases, particularly parasitic or viral, in which the disease agent remains hidden and dormant within host cells for prolonged periods.

The microsphere compositions of this invention are also valuable for diagnostic medical and biochemical analyses. When modified appropriately with such substances as polypeptides, antibodies, antigens, enzymes, enzyme substrates, and radiolabeled or modified with fluorescent compounds, they may be readily designed to provide highly sensitive systems for radioimmune assays or fluorescence assays to detect a wide range of disease conditions. Important among such diagnostic tests are assays to detect cancer and venereal disease as well as parasitic, viral fungal and bacterial infections. The microporous, particulate, hydrophilic nature of the microspheres of this invention make them readily modifiable for such diagnostic applications by covalent attachment or physical association of specific-binding biological substances. Biospecific affinity chromatography, i.e., for separation of specific antibodies, antigens, enzymes and other metabolites, is similarly also an important application for the hydrophilic protein and polypeptide microspheres of this invention.

We claim:

1. A method of preparing novel hydrophilic microspheres consisting essentially of cross-linked protein or polypeptide comprising
   (a) providing a dispersion of an aqueous solution or dispersion of polypeptide or protein microspheres in an organic, substantially water immiscible solvent solution of a high molecular weight polymer, said organic solvent being substantially a non-solvent for said microspheres and said polymer solution stabilizing the dispersion of microspheres,
   (b) incorporating a polyfunctional cross-linking agent for said protein or polypeptide in the organic phase of said dispersion, and
   (c) allowing said cross-linking agent to react with said protein or polypeptide microspheres for a time sufficient to cross-link at least a portion of the microspheres, thereby providing microspheres containing free reactive functional groups.

2. The method of claim 1 including the step of separating said cross-linked protein or polypeptide microspheres from said dispersion.

3. The method of claim 1 wherein said protein is albumin.

4. The method of claim 3 wherein said albumin is human serum albumin.

5. The method of claim 3 wherein said albumin is bovine serum albumin.

6. The method of claim 1 or 2 wherein said organic solvent solution of high molecular weight polymer is a solution of polymethylmethacrylate in a mixture of toluene and chloroform.

7. The method of claim 1 or 2 wherein said organic solvent solution of high molecular weight polymer is a solution of polyoxyethylene-polyoxypropylene copolymer in chloroform.

8. The method of claim 1 or 2 wherein said organic solvent solution of high molecular weight polymer is a solution of cellulose acetate butyrate in ethylene dichloride.

9. The method of claim 1 or 2 wherein said organic solvent solution of high molecular weight polymer is a solution of bisphenol polycarbonate in chloroform.

10. The method of claim 1 or 2 wherein the concentration of high molecular weight polymer in organic solvent is from about 1% to about 40%, by weight.

11. The method of claim 1 or 2 wherein said stabilized dispersion of protein or polypeptide microspheres is formed by dispersing an aqueous solution of said protein or polypeptide in said organic solvent solution of high molecular weight polymer.

12. The method of claim 1 or 2 wherein said microspheres have an average size in the range of from about 0.05 microns to about 500 microns.

13. The method of claim 1 or 2 wherein said cross-linking agent is a dialdehyde.

14. The method of claim 13 wherein said cross-linking agent is glutaraldehyde.

15. The method of claim 1 or 2 wherein said cross-linking agent is a diisocyanate.

16. The method of claim 15 wherein said diisocyanate is 2,4-tolylene diisocyanate or 1,6-diisocyanate hexane.

17. The product produced according to the method of claim 1 or 2.

18. The product produced according to the method of claim 3.

19. The method of claim 1 or 2 including the step of reacting reactive functional groups of said cross-linked microspheres with a first substance containing at least one functional group reactive therewith to form a covalent bond between said cross-linked microspheres and said substance.

20. The method of claim 19 wherein said first substance is a biologically active substance suitable for administration to a biological system.

21. The method of claim 19 wherein said substance contains at least one additional functional group which is non-reactive with the reactive functional groups of said cross-linked microspheres.

22. The method of claim 21 wherein said at least one additional functional group is reacted with a second substance containing a functional group reactive therewith to form a bond therebetween.

23. The method of claim 22 wherein said second substance is a biologically active substance suitable for administration to a biological system.

24. The product produced according to the method of claim 19.

25. The product produced according to the method of claim 20.

26. The product produced according to the method of claim 21.

27. The product produced according to the method of claim 22.

28. The product produced according to the method of claim 23.

29. A composition in unit dosage form adapted for administration to a biological system comprising a biologically effective amount of the product of any of claims 24 to 28 and a biologically acceptable carrier therefor.

30. A method of administering a biologically active substance to a biological system comprising administering thereto the product of any of claims 24 to 28.

* * * * *